United States Patent
Fujita et al.

(10) Patent No.: US 9,551,664 B2
(45) Date of Patent: Jan. 24, 2017

(54) LASER SCANNING MICROSCOPE SYSTEM

(71) Applicant: Sony Corporation, Tokyo (JP)

(72) Inventors: Goro Fujita, Kanagawa (JP); Masaaki Hara, Kanagawa (JP)

(73) Assignee: Sony Corporation, Tokyo (JP)

(*) Notice: Subject to any disclaimer, the term of this patent is extended or adjusted under 35 U.S.C. 154(b) by 65 days.

(21) Appl. No.: 14/279,934

(22) Filed: May 16, 2014

(65) Prior Publication Data
US 2014/0353521 A1    Dec. 4, 2014

(30) Foreign Application Priority Data
May 30, 2013    (JP) .................. 2013-113572

(51) Int. Cl.
G01N 1/30    (2006.01)
G01N 21/64    (2006.01)

(52) U.S. Cl.
CPC .................. *G01N 21/6458* (2013.01)

(58) Field of Classification Search
CPC  G01N 21/8806; G01N 21/6458; G01N 21/65; G01N 1/30
USPC .................. 250/458.1, 459.1, 205, 201.3
See application file for complete search history.

(56) References Cited

U.S. PATENT DOCUMENTS

| | | | | |
|---|---|---|---|---|
| 4,794,598 A * | 12/1988 | Desurvire | ............... | H01S 3/302 372/3 |
| 5,252,834 A * | 10/1993 | Lin | .................. | G01N 21/6408 250/458.1 |
| 5,982,535 A * | 11/1999 | Inoue | .................. | G02B 21/26 359/368 |
| 7,554,722 B2 * | 6/2009 | Widzgowski | ...... | G02B 21/0032 250/205 |
| 8,630,322 B2 * | 1/2014 | Dantus | ................. | H01S 3/0057 372/24 |
| 8,735,790 B2 * | 5/2014 | Schulte | ............. | G02B 21/0032 250/201.3 |
| 2001/0015411 A1 * | 8/2001 | Ohdaira | ............... | G02B 21/002 250/458.1 |
| 2002/0149396 A1 * | 10/2002 | Mizuhara | ................. | G01J 1/44 327/1 |
| 2002/0153470 A1 * | 10/2002 | Kumagai | ............. | G01C 15/002 250/206.2 |
| 2005/0112541 A1 * | 5/2005 | Durack | ............... | C12N 5/0612 435/2 |

(Continued)

FOREIGN PATENT DOCUMENTS

JP    5007092    8/2012

*Primary Examiner* — David Porta
*Assistant Examiner* — Djura Malevic
(74) *Attorney, Agent, or Firm* — K&L Gates LLP (57) ABSTRACT

There is provided a laser scanning microscope system including a mode-locked laser unit configured to radiate a laser beam with a predetermined frequency, an intermittent light-emitting unit configured to intermittently emit the laser beam radiated from the mode-locked laser unit in a predetermined intermittent light-emission period, a detector configured to convert a fluorescent substance into an electric signal, the fluorescent substance receiving the intermittently emitted laser beam and then being excited from an object, and an A/D conversion unit configured to sample the electric signal in a sampling period synchronized with the intermittent light-emission period.

9 Claims, 8 Drawing Sheets

(56) References Cited

U.S. PATENT DOCUMENTS

2014/0172345 A1\* 6/2014 Stoker ................ G01R 31/311
  702/117
2015/0056645 A1\* 2/2015 Vacca ................ G01N 15/1459
  435/29

\* cited by examiner

LASER SCANNING MICROSCOPE SYSTEM

CROSS REFERENCES TO RELATED APPLICATIONS

The present application claims priority to Japanese Priority Patent Application JP 2013-113572 filed in the Japan Patent Office on May 30, 2013, the entire content of which is hereby incorporated by reference.

BACKGROUND

The present disclosure relates to a laser scanning microscope system.

In the related art, for example, Japanese Patent No. 5007092 discloses a scanning microscope that includes a scanning device scanning an object and performs synchronization between an oscillation pulse frequency and a sampling frequency.

SUMMARY

In recent years, microscopes having a high output equal to or greater than 100 W due to an MOPA type light source using a semiconductor laser have been developed. However, in a case in which a biological object is a measurement target, a powerful laser beam unfortunately damages the biological object.

In order to suppress the damage to the biological object, it is effective to lower an average power of a laser beam and increase a peak power. For this reason, the damage to the biological object can be considered to be suppressed by emitting a laser beam intermittently.

In laser scanning microscopes, however, excited fluorescent substances in objects are converted into electric signals by detectors such as PMTs. However, when a laser beam is emitted intermittently, an acquired image may unfortunately deteriorate depending on sampling of A/D conversion after conversion.

In Japanese Patent No. 5007092, it is described that the synchronization between the oscillation pulse frequency and the sampling frequency is performed. However, an intermittent light-emission period when intermittent light emission is performed is not mentioned. Further, in the technology disclosed in Japanese Patent No. 5007092, even when high-speed sampling is performed in synchronization with pulse light emission, an improvement in resolution is not realized and it is also difficult to increase a signal amount.

Accordingly, it is desirable to suppress deterioration in an image by optimally sampling an electric signal by an excited fluorescent substance in an object when a laser beam is emitted intermittently.

According to an embodiment of the present disclosure, there is provided a laser scanning microscope system including a mode-locked laser unit configured to radiate a laser beam with a predetermined frequency, an intermittent light-emitting unit configured to intermittently emit the laser beam radiated from the mode-locked laser unit in a predetermined intermittent light-emission period, a detector configured to convert a fluorescent substance into an electric signal, the fluorescent substance receiving the intermittently emitted laser beam and then being excited from an object, and an A/D conversion unit configured to sample the electric signal in a sampling period synchronized with the intermittent light-emission period.

Frequencies and phases related to the sampling and the intermittent light emission may be the same.

The mode-locked laser unit may radiate the laser beam for two-photon excitation.

A sampling signal providing the sampling period to the A/D conversion unit and an intermittent light-emission signal providing the intermittent light-emission period to the intermittent light-emitting unit may be the same signal.

The laser scanning microscope system may further include a sampling signal generation unit configured to generate a sampling signal providing the sampling period to the A/D conversion unit, and an intermittent light-emission signal generation unit configured to generate an intermittent light-emission signal providing the intermittent light-emission period to the intermittent light-emitting unit. The sampling signal and the intermittent light-emission signal may be generated based on an identical clock.

The mode-locked laser unit or the intermittent light-emitting unit may cause the laser beam to be incident on the object only during a predetermined effective light-emission period.

The laser scanning microscope system may further include a first galvanomirror configured to perform scanning with the laser beam in a first direction of a surface of the object, a second galvanomirror configured to perform scanning with the laser beam in a second direction orthogonal to the first direction of the surface of the object, and a galvanomirror control unit configured to control the first galvanomirror and the second galvanomirror. When the scanning in the first direction is completed, the galvanomirror control unit may return the laser beam to a start position of the first direction and may perform the scanning in the second direction by one line of the laser beam, and may then perform the scanning in the first direction again. The effective light-emission period may be at least a part of a period in which the scanning in the first direction is performed.

The laser scanning microscope system may further include a lowpass filter configured to perform band limitation on the electric signal output from the detector and to input the electric signal to the A/D conversion unit. The lowpass filter may perform the band limitation in a manner that a Nyquist sampling theorem is established for a frequency of the sampling.

The lowpass filter may perform the band limitation in a manner that the band limitation is equal to or less than ½ of the frequency of the sampling.

According to embodiments of the present disclosure, it is possible to suppress deterioration in an image by optimally sampling an electric signal by an excited fluorescent substance in an object when a laser beam is emitted intermittently.

Additional features and advantages are described herein, and will be apparent from the following Detailed Description and the figures.

DETAILED DESCRIPTION

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

The description will be made in the following order.

1. Microscope system
2. Example of configuration of light source
3. Example of the configuration of microscope system
4. Relation between sampling period and intermittent light-emission period
5. Example of configuration in which sampling period is caused to be identical to intermittent driving period
6. Configuration of lowpass filter
7. Synchronization between optical pulse of laser beam and modulation of laser beam
8. Relation between optical resolution and sampling frequency

[1. Microscope System]

Figure 1:
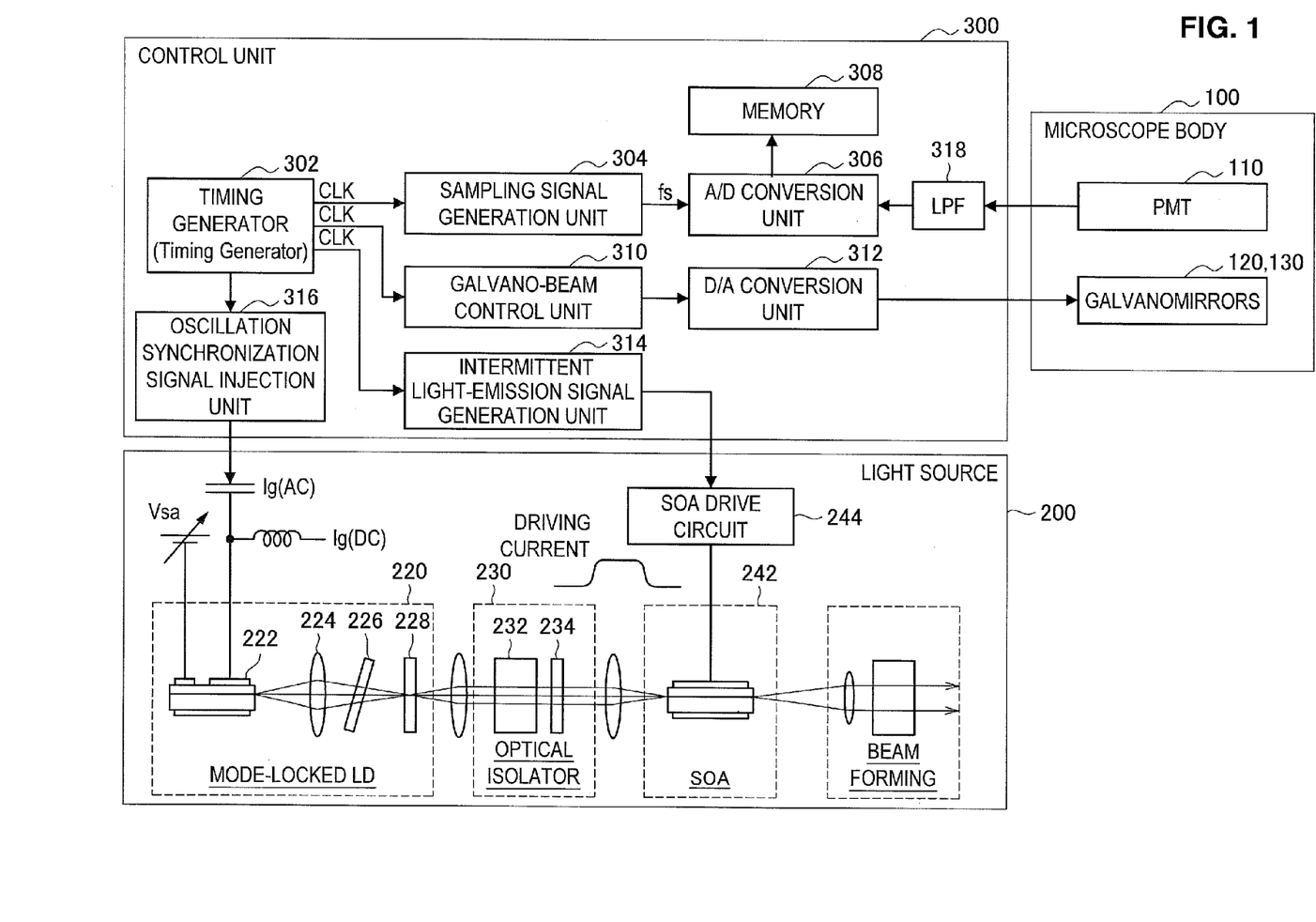
FIG. 1 is a schematic diagram illustrating an example of a microscope system according to an embodiment of the present disclosure.

First, a microscope system according to an embodiment of the present disclosure will be described with reference to FIG. 1. FIG. 1 is a schematic diagram illustrating an example of the microscope system according to the embodiment. The microscope system is a laser scanning microscope for biological analysis and is particularly a microscope system including a two-photon excitation light source. As illustrated in FIG. 1, a microscope system 1000 is configured to include a microscope body 100, a light source 200, and a control unit 300.

The microscope body 100 is configured as a laser scanning microscope and scans a measurement sample S 3-dimensionally in the vertical direction, the horizontal direction, and the depth direction of the measurement sample to generate an image data group corresponding to an expanded image group of the measurement sample S. Therefore, the microscope body 100 is configured to include a photomultiplier tube (PMT) and galvanomirrors. The configuration of the microscope body 100 will be described in detail below.

The light source 200 uses a pulse laser and is a master oscillator power amplifier (MOPA) type light source configured to include a laser (mode-locked laser diode (hereinafter referred to as an MLLD)) including an external resonator and a semiconductor optical amplifier (SOA). In recent years, microscopes having a high output equal to or greater than 100 W due to an MOPA type light source using a semiconductor laser have been developed. The light source has characteristics including a low price and a small size. Therefore, when the light source can be mounted on a multi-photon microscope of a middle range, its applicability in a wide variety of research organizations is increased, and thus considerable contribution can be expected in medical and pharmaceutical fields. In the embodiment, a microscope system using such an MOPA type light source, in particular, a microscope system using a two-photon excitation light source, will be described.

The control unit 300 has a function of controlling the microscope body 100 and the light source 200. The configuration of the control unit 300 will be described in detail below.

[2. Example of Configuration of Light Source]

Figure 2:
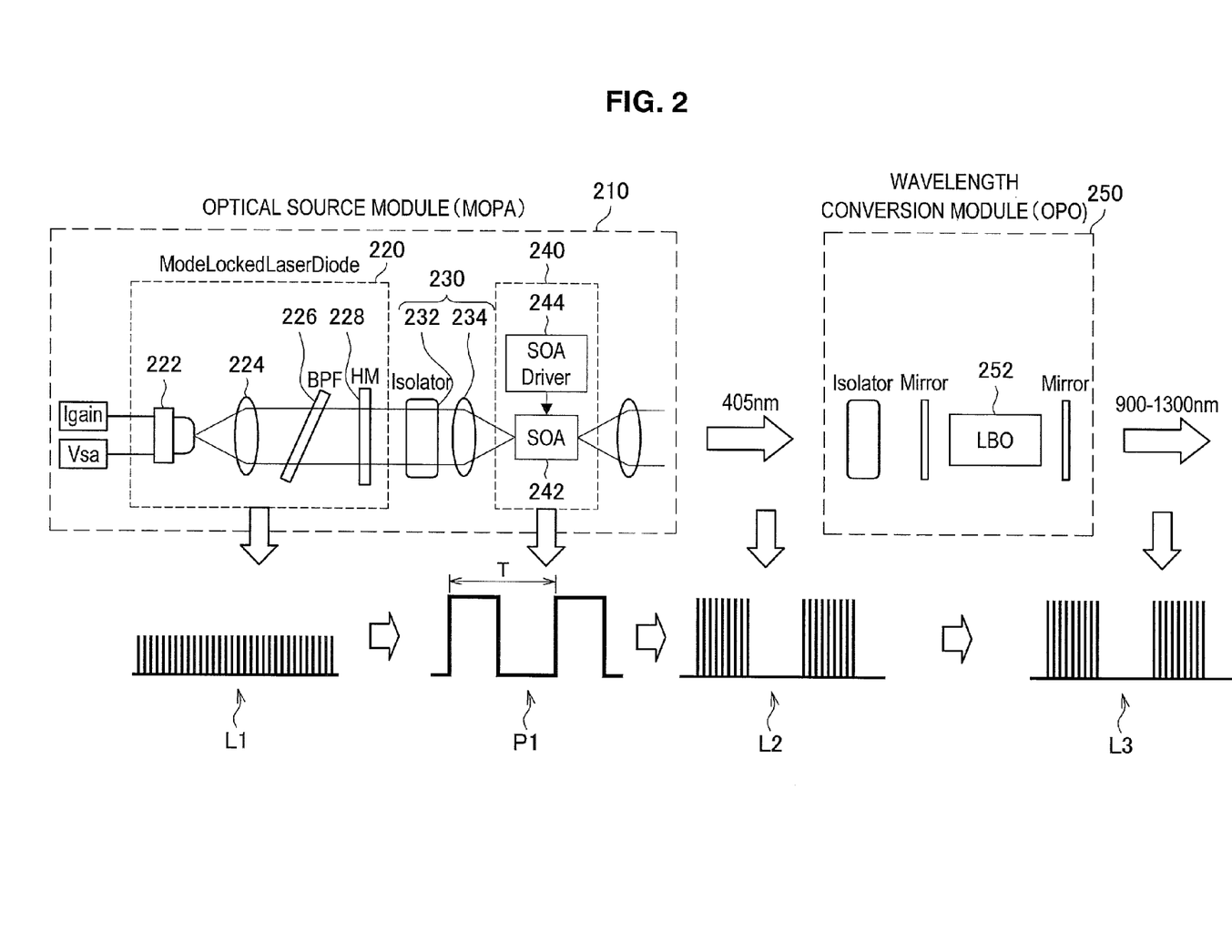
FIG. 2 is a schematic diagram illustrating the configuration of a light source in detail.

FIG. 2 is a schematic diagram illustrating the configuration of the light source 200 in detail. The light source 200 is configured to include an MOPA 210 in which a mode-locked oscillation type laser and an optical amplifier are combined and a wavelength conversion module (OPO) 250. The MOPA 210 includes a mode-locked laser unit (mode-locked laser diode) 220, an optical isolator unit 230, and an optical amplifier unit (SOA unit) 240.

The lower portion of FIG. 2 illustrates pulse waveforms L1, L2, and L3 of laser beams output from the mode-locked laser unit 220, the optical amplifier unit 240, and the wavelength conversion module 250 and a pulse waveform P1 for intermittent driving to be described below.

The mode-locked laser unit 220 is configured to include a semiconductor laser 222 and elements, i.e., a lens 224, a bandpass filter 226, and a mirror 228 that pass the laser beam radiated from the semiconductor laser 222. The bandpass filter 226 has a function of transmitting light within a given wavelength range and not transmitting light out of the range. An external resonator (space resonator) is configured between a rear-side mirror of the semiconductor laser 222 and the mirror 228, and the frequency of the laser beam radiated from the mode-locked laser unit 220 is decided by a path length of the external resonator. Thus, since the frequency of the laser beam can be forcibly locked to a specific frequency, a mode of the laser beam can be locked.

The mode-locked laser unit 220 can synchronize a short pulse with a period (for example, about 1 GHz) longer than a normal semiconductor laser by configuring the external resonator. Therefore, a laser beam L1 output from the mode-locked laser unit 220 has low average power and a high peak, and thus damage to a biological object becomes small and photon efficiency becomes high.

The optical isolator unit 230 is disposed on the rear stage of the mode-locked laser unit 220. The optical isolator unit 230 is configured to include an optical isolator 232 and a mirror 234. The optical isolator unit 230 has a function of preventing light reflected from an optical component or the like on the rear stage from being incident on the semiconductor laser 222.

The optical amplifier unit (SOA unit) 240 functions as an optical modulation unit that amplifies and modulates the laser beam radiated from the semiconductor laser 222 and is disposed on the rear stage of the optical isolator unit 230. Since the laser beam output from the mode-locked laser unit 220 has relatively small power, the laser beam is amplified by the optical amplifier unit 240. The optical amplifier unit 240 is configured to include a semiconductor optical amplifier (SOA), i.e., a semiconductor optical amplifier 242 and an SOA driver 244 controlling the semiconductor optical amplifier 242. The semiconductor optical amplifier 242 is an optical amplifier with a small size and a low cost and can be used as an optical gate and a light switch turning light on and off. In the embodiment, the laser beam radiated from the semiconductor laser 222 is modulated by ON and OFF of the semiconductor optical amplifier 242.

In the optical amplifier unit (SOA unit) 240, the laser beam is amplified according to the magnitude of a control current (direct current). Further, the optical amplifier unit 240 turns the laser beam on and off with the pulse waveform L1 in a predetermined period T by performing intermittent driving by the control current with the pulse waveform P1 illustrated in FIG. 2 at the time of the amplification and outputs an intermittent laser beam (the pulse waveform L2). By generating the pulse waveform with a desired timing and period in this way, it is possible to realize synchronization with a control signal which the system has. Thus, for example, in the case of the MOPA type light source, intermittent driving can be realized by performing intermittent driving in the semiconductor optical amplifier 242 (in which a semiconductor optical amplifier is abbreviated to an SOA) on the rear stage that amplifies the pulse of an oscillation unit on the front stage. In the case of the MOPA type light source, the optical amplifier unit 240 (the semiconductor optical amplifier 242) functions as an intermittent light-emitting unit.

In the embodiment, since the MLLD is used, the frequency of the laser beam output from the semiconductor laser 222 is, for example, in the range of about 500 MHz to about 1 GHz and the pulse width thereof is in the range of about 0.5 [ps] to about 1.0 [ps]. As will be described below, by injecting a transmission synchronization signal from an oscillation synchronization signal injection unit 316, an oscillation pulse output from the semiconductor laser 222 can also be synchronized with the control signal which the system has in addition to the synchronization of the intermittent driving by the SOA unit. Also, when TiSa is used, the oscillation frequency of the laser beam is in the range of about 40 MHz to about 80 MHz and the pulse width thereof is in the range of about 0.1 [ps] to about 0.2 [ps]. On the other hand, by using the MLLD, it is possible to output the laser beam with a higher oscillation frequency.

In the embodiment, the wavelength of the laser beam output from the optical amplifier unit 240 is, for example, 405 nm. Since the wavelength of 405 nm is a wavelength in which optical absorption is large, the wavelength is converted into a wavelength (about 900 nm to about 1300 nm) reaching the inside of a biological object and producing a two-photon effect at a high density. For this reason, the laser beam output from the optical amplifier unit 240 is input to the wavelength conversion module 250 on the rear stage, so that the wavelength thereof is converted by an LBO 252 of the wavelength conversion module 250.

For example, the LBO 252 of the wavelength conversion module 250 converts the input laser beam (the pulse waveform L2) into two wavelengths. Then, of the two converted wavelengths, the laser beam (the pulse waveform L3) with the longer wavelength is output from the wavelength conversion module 250. In the embodiment, the wavelength conversion module 250 is not an indispensable constituent element and an object (the measurement sample S) can also be irradiated using the laser beam output from the optical amplifier unit 240 as final light.

Incidentally, in observation of a biological object with a laser microscope, in order to reduce damage to the object, it is effective to lower average power of a laser and increase peak power of the laser. Also, a laser chip included in the MOPA type light source using a semiconductor laser is small in size, and therefore an operational limitation is considered to be imposed due to heat generation caused by a load of high power.

Since the light source 200 according to the embodiment outputs an intermittent laser beam (the pulse wavelength L2) and performs an intermittent operation, a peak at the time of the light emission can be increased despite the fact that the average power is the same, compared to a case in which the intermittent operation is not performed. Also, by performing the intermittent operation, it is possible to suppress heat generation caused by a load of high power.

In the embodiment, the light source 200 used as the two-photon excitation light source 200 excites a fluorescent substance with two photons. In particular, in a microscope using a two-photon excitation light source, a figure of merit FOM (=(Peak Power)$^2$×Pulse Width×Frequency=Peak Power×Average Power) is known. According to the figure of merit, an output can be increased in proportion to a product of peak power and average power. Accordingly, in observation of a biological object with a laser microscope, in order to suppress damage to an object to be as small as possible and increase an output, it is effective to lower the average power and to increase the peak power. Therefore, in the embodiment, a duty (DUTY=Pulse Width×Frequency) ratio is lowered and the peak power is increased by performing the intermittent operation.

Figure 3:
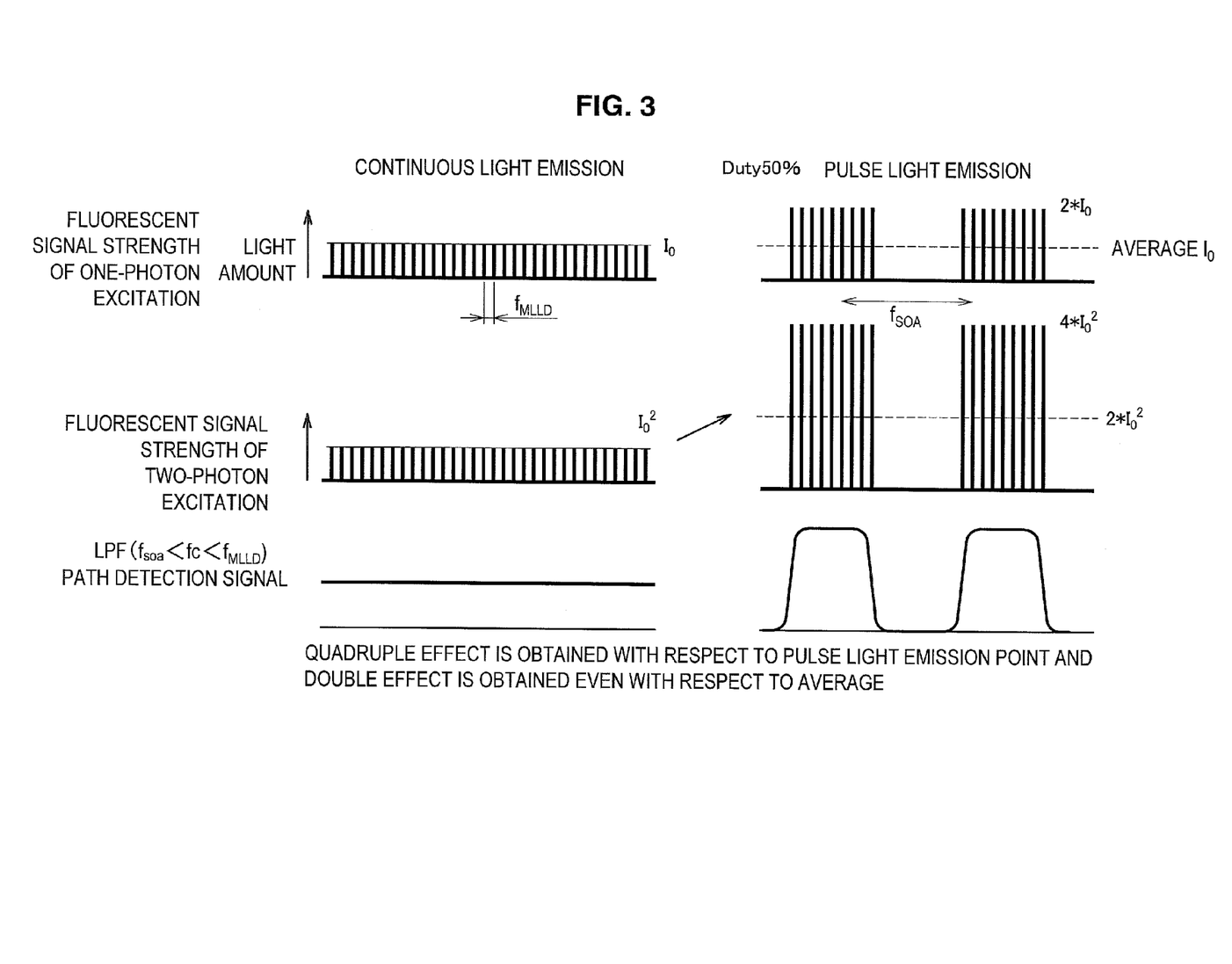
FIG. 3 is a diagram illustrating characteristics when peak power of a laser is increased by intermittent light emission.

FIG. 3 is a diagram illustrating characteristics when the peak power of the laser is increased by intermittent light emission. The upper portion of FIG. 3 illustrates characteristics in the case of one-photon excitation. The characteristics on the left side of the upper portion show peak power of continuous light emission and the characteristics on the right side thereof show peak power of intermittent light emission when the DUTY ratio is set to 50%. Thus, when the DUTY ratio of the intermittent light emission is set to 50%, a signal strength ($2 \times I_0$) twice a signal strength ($I_0$) of the continuous light emission can be output in the case of the intermittent light emission.

The middle portion of FIG. 3 illustrates characteristics in the case of the two-photon excitation. The characteristics on the left side show peak power of the continuous light emission and the characteristics on the right side show peak power of the intermittent light emission when the DUTY ratio is set to 50%. The figure of merit FOM is increased by a square of the peak power in the case of the two-photon excitation. Accordingly, in the case of the intermittent light emission, a signal strength ($=4 \times I_0^2$) of the two-photon excitation is four times a signal intensity ($=I_0^2$) of the continuous light emission. Also, even in an average signal strength of a pulse light emission point and a pulse non-light emission point, an average signal strength ($=2 \times I_0^2$) of the two-photon excitation is twice the signal intensity ($=I_0^2$) of the continuous light emission. Accordingly, in the embodiment, by performing the intermittent driving in the two-photon excitation light source 200, it is possible to increase the peak power and the average signal strength.

The characteristics of the lower portion of FIG. 3 show a signal obtained by passing the characteristics of the middle portion through a lowpass filter (a lowpass filter (LPF) 318) illustrated in FIG. 1) of the band limitation. A process performed by the lowpass filter of the band limitation is performed before A/D conversion. Therefore, when a duty ratio of ON/OFF is 50% (1/2), a signal amplitude before the A/D conversion becomes 1/2. Consequently, a double signal amplitude can be obtained in the intermittent light emission of the two-photon excitation. Also, when the duty ratio of ON/OFF is 1/n and the peak power becomes n times, the signal amplitude obtained by the two-photon excitation becomes n times. Therefore, the duty is preferably small. However, in practice, since there is the upper limit in the peak power obtained from the light source 200, it is appropriate to select an appropriate value equal to or less than 1 as the duty ratio.

[3. Example of the Configuration of Microscope System]

Figure 4:
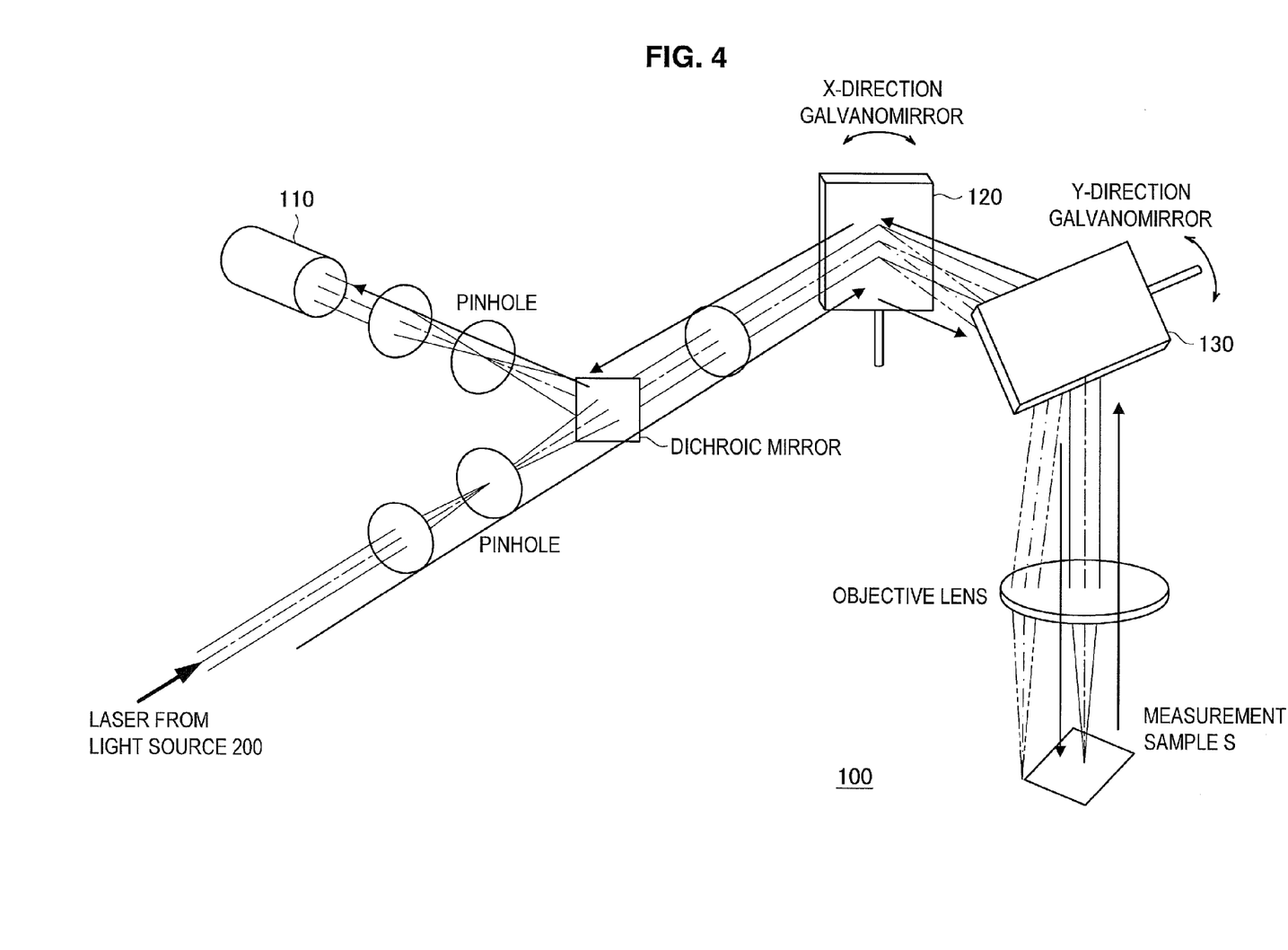
FIG. 4 is a schematic diagram illustrating the configuration of a microscope body.

Next, the configuration of the microscope body 100 will be described with reference to FIG. 4. FIG. 4 illustrates an example of the configuration of a confocal fluorescence microscope using two kinds of galvanomirrors. The microscope body 100 performs beam scanning on the target sample S two-dimensionally by the two galvanomirrors.

Excitation light radiated from the light source 200 passes through pinholes that are installed in an optical system such as a lens and at a conjugated position, and subsequently passes through a dichroic mirror that passes excitation light and reflects fluorescence. The excitation light having passed through the dichroic mirror passes through an optical system such as a lens so that the X coordinate is controlled by an X-direction galvanomirror 120 that controls scanning in the X direction of the measurement sample and the Y coordinate is subsequently controlled by a Y-direction galvanomirror 130 that controls scanning in the Y direction, and then is condensed at desired XY coordinates on the measurement sample S by an objective lens.

The fluorescence emitted from the measurement sample is reflected by the Y-direction galvanomirror 130 and the X-direction galvanomirror 120, traces the same path as that of the excitation light, and is reflected by the dichroic mirror. The fluorescence reflected by the dichroic mirror passes through the pinhole installed at the conjugated position, and is subsequently guided to a detector 110 such as a photomultiplier tube (PMT).

Here, the rotation shafts of the two galvanomirrors used to control a condensing position on the measurement sample are connected to mirrors, as schematically illustrated in FIG. 4. In the galvanomirrors 120 and 130, rotation amounts of the rotation shafts are controlled according to the magnitude of an input voltage and angles at which the mirror surfaces face can be changed at a high speed and with high precision.

FIG. 4 illustrates the case of the one-photon excitation. In the case of the two-photon excitation, since it is not necessary to pass the light through the galvanomirrors and the pinholes, the fluorescence emitted from the measurement sample may be guided to the detector such as a photomultiplier tube (PMT) installed on the rear stage of the objective lens.

In the laser scanning microscope illustrated in FIG. 4, the ways in which excitation light moves when the XY plane of the measurement sample is scanned are different according to a combination of operation methods of the two galvanomirrors 120 and 130. Hereinafter, a method of generating a two-dimensional image using a raster scanning scheme which is the most general scanning scheme will be described with reference to FIG. 5. In the case of the raster scanning scheme, scanning is performed in the horizontal direction with the X-direction galvanomirror 120 and return light to the detector 110 is sampled at a central portion other than the returned vicinity to be set as image information.

Figure 5:
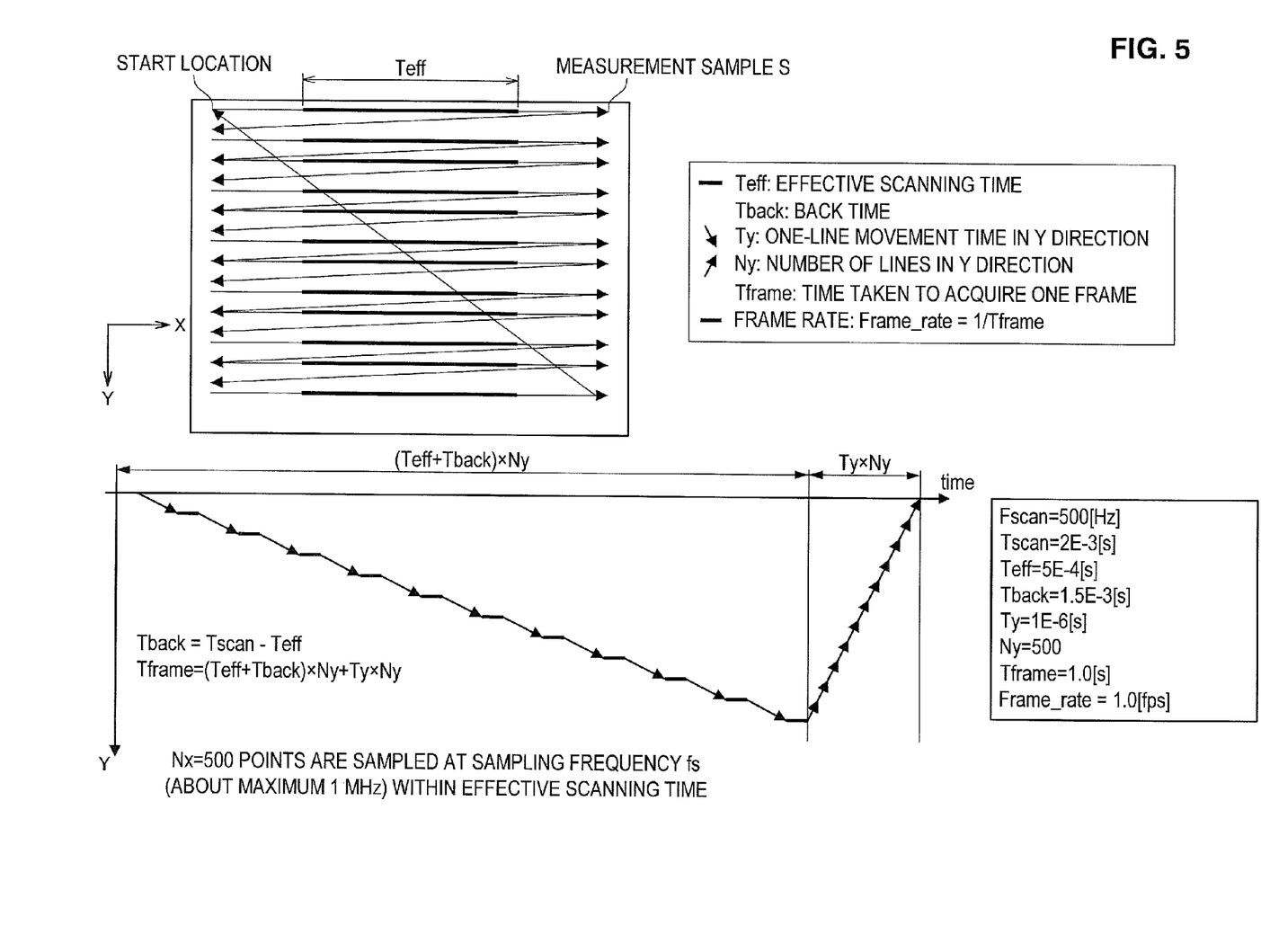
FIG. 5 is a schematic diagram illustrating a method of generating a 2-dimensional image using a raster scanning scheme.

In the following description, for example, on the sample plane of the measurement sample S on which the coordinate system illustrated in FIG. 5 is defined, an operation speed of the galvanomirror 120 controlling the scanning in the X direction is assumed to be faster than an operation speed of the galvanomirror 130 controlling the scanning in the Y direction.

The drawing illustrated in the upper portion of FIG. 5 schematically shows how the excitation light moves in the XY directions when the top left location of the sample plane is assumed to be a start point of the scanning.

In the raster scanning scheme, as shown on the sample plane of the measurement sample S in FIG. 5, detection of the fluorescence (acquisition of an image) is performed during a period in which the X-direction galvanomirror 120 is rotated so that the excitation light is moved in the X direction from the left end to the right end of the sample plane. In the raster scanning scheme, the Y-direction galvanomirror 130 stops during the period in which the X-direction galvanomirror 120 operates.

Basically, when the excitation light reaches up to the right end of the sample plane, the detection of the fluorescence is paused and the X-direction galvanomirror 120 changes a rotation angle of the rotation shaft up to a position corresponding to the left end. During this period, the Y-direction galvanomirror 130 moves a step in the Y axis positive direction by one line. When such an operation is repeated by the number of lines and the excitation light reaches up to the bottom right of the sample plane, the X-direction galvanomirror 120 and the Y-direction galvanomirror 130 return the position to the start position of the scanning by rotating each rotation shaft considerably so that one two-dimensional image (frame) is generated.

In such a raster scanning scheme, the Y-direction galvanomirror 130 stops while the X-direction galvanomirror 120 operates. Therefore, a shape of a unit (image formation unit) in which the generated two-dimensional image is formed is a rectangular shape illustrated in the upper portion of FIG. 5.

The graph illustrated in the lower portion of FIG. 5 is a timing chart showing how the Y coordinate changes over time. When $T_{frame}$ is a time necessary to obtain a one-frame image, the time is expressed as in the following equation 11, as apparent from the timing chart in the lower portion of FIG. 5. Here, in the following equation 11, $T_{scan}$ indicates a scanning period, $N_y$ indicates the number of lines in the Y direction, and $T_{Y\_all}$ indicates a return time in the Y direction.

$$T_{frame} = (T_{scan}) \times N_y + T_{Y\_all} \quad \text{(equation 11)}$$

Here, the scanning period $T_{scan}$, an effective scanning time $T_{eff}$, and a back time $T_{back}$ have a relation expressed in the following equation 12. When $T_y$ is a one-line movement time in the Y direction, the return time $T_{Y\_all}$ in the Y direction is expressed as in the following equation 13. Here, the back time $T_{back}$ in the following equation 12 indicates a total time necessary for movement from the end of the effective scanning section (for example, a section indicated by a solid line in the X direction on the sample plane in the upper portion of FIG. 5) to the start of the effective scanning section of the subsequent period.

$$T_{eff} = T_{scan} - T_{back} \quad \text{(equation 12)}$$

$$T_{Y\_all} = T_y \times N_y \quad \text{(equation 13)}$$

For example, a case in which the scanning frequency $F_{scan}$ of the X-direction galvanomirror 120 is 7.8 kHz will be considered. In this case, the scanning period $T_{scan}$ is expressed as a reciprocal of the scanning frequency $F_{scan}$, $T_{scan} = 1/F_{scan} = 1.28 \times 10^{-4}$ seconds. Also, when the effective scanning time $T_{eff}$ of this galvanomirror is expressed as $\{\text{scanning period } T_{scan} \times (1/3)\}$ based on scanning efficiency, the effective scanning time is $4.27 \times 10^{-5}$ seconds and the back time $T_{back}$ is $1.28 \times 10^{-4} - 4.27 \times 10^{-5} = 8.53 \times 10^{-5}$ seconds.

Also, when the return time Ty in the Y direction in the Y-direction galvanomirror 130 is $1 \times 10^{-6}$ and the number of lines $N_y$ in the Y direction is 512, the time $T_{frame}$ necessary to photograph one frame is $6.62 \times 10^{-2}$ seconds from the foregoing equation 11. Since the frame rate is a value expressed as a reciprocal of $T_{frame}$, Frame-rate=15.1 (frame/s) in such a scanning system.

In the raster scanning scheme illustrated in FIG. 5, as shown in the sample plane in the upper portion of FIG. 5, in a period in which the X-direction galvanomirror 120 is rotated and the excitation light is moved in the X direction from the left end to the right end of the sample plane, the light source 200 is caused to emit light only during the effective scanning time $T_{eff}$. That is, in the round-trip scanning in the X direction, the light source 200 is turned on only during the effective scanning time $T_{eff}$ in which the image is acquired and the light source is turned off during a period other than the effective scanning time $T_{eff}$ and a direction change period. At this time, the ON/FF of the light source 200 is performed at a frequency in the range of about 50 Hz to about 10 kHz. Therefore, since the light is emitted periodically by causing the light source 200 to emit light only during the effective scanning time $T_{eff}$ as well as the intermittent driving by the above-described pulse waveform P1, the average power of the laser can be lowered and the peak power can be increased.

Also, when the microscope body 100 is not in an image acquisition mode, the light source 200 is assumed to be turned off. At this time, the light source 200 may be turned off by turning off the optical amplifier unit 240, or the MLLD itself may be turned off.

[4. Relation Between Sampling Period and Intermittent Light-Emission Period]

Figure 6:
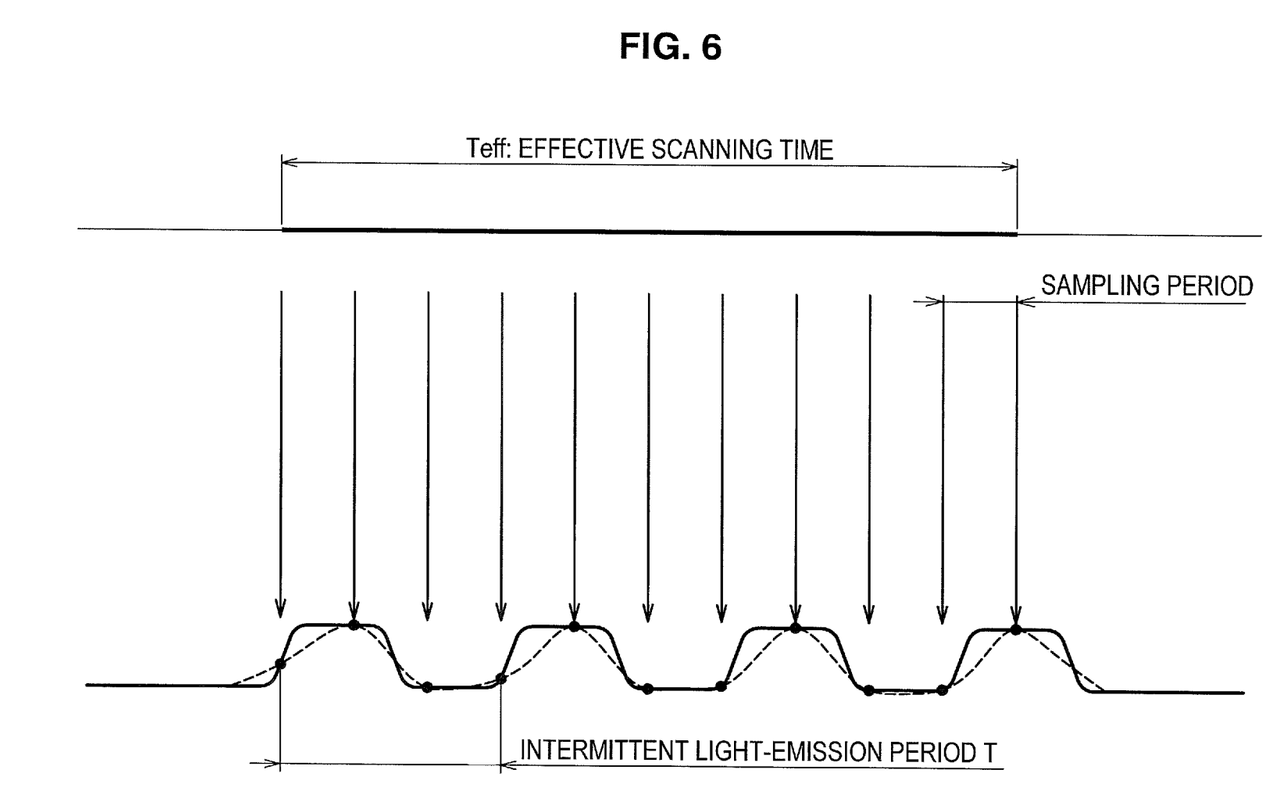
FIG. 6 is a schematic diagram illustrating a case in which a sampling period is shorter than an intermittent light-emission period T.
Figure 7:
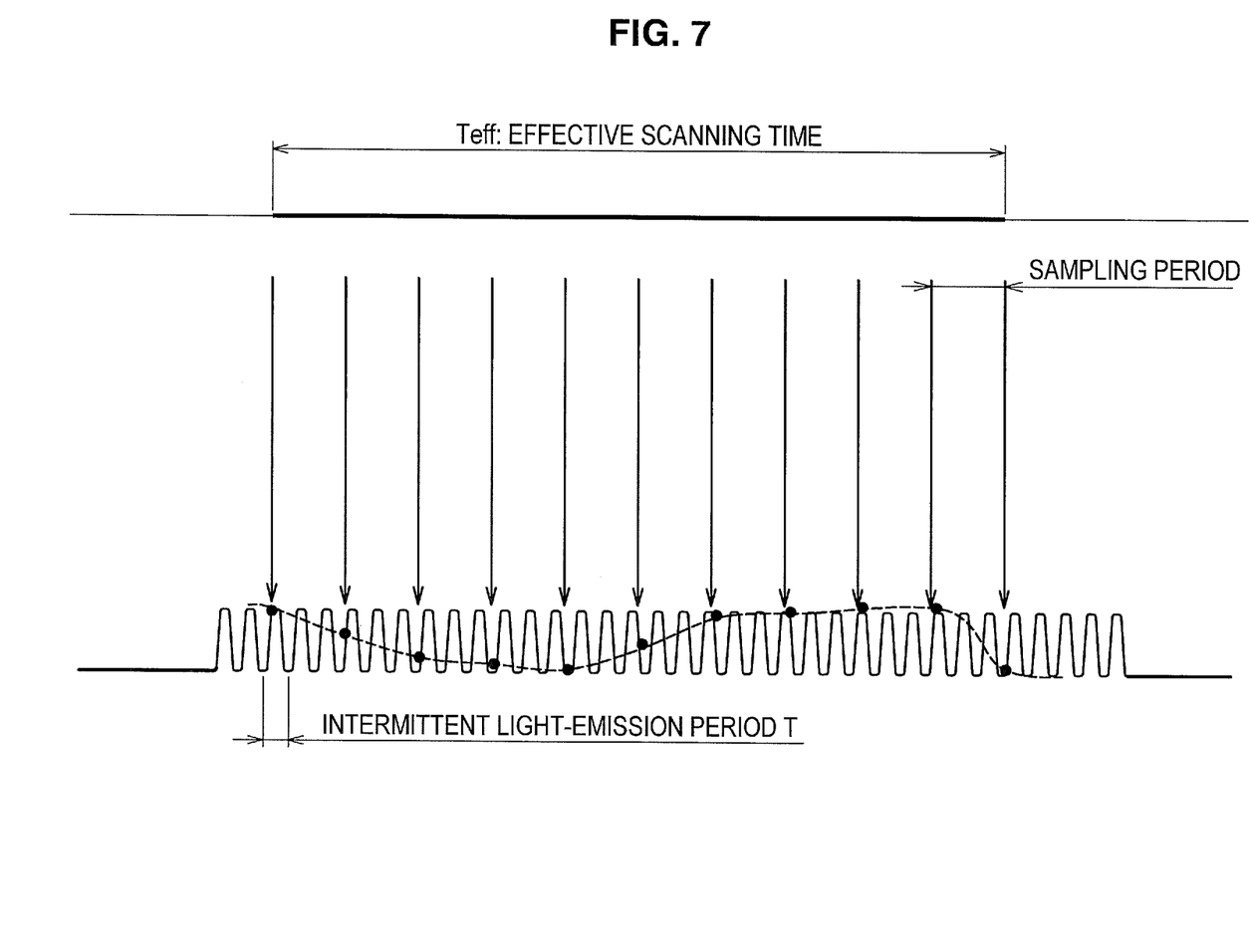
FIG. 7 is a schematic diagram illustrating a case in which a sampling period is longer than an intermittent light-emission period T.
Figure 8:
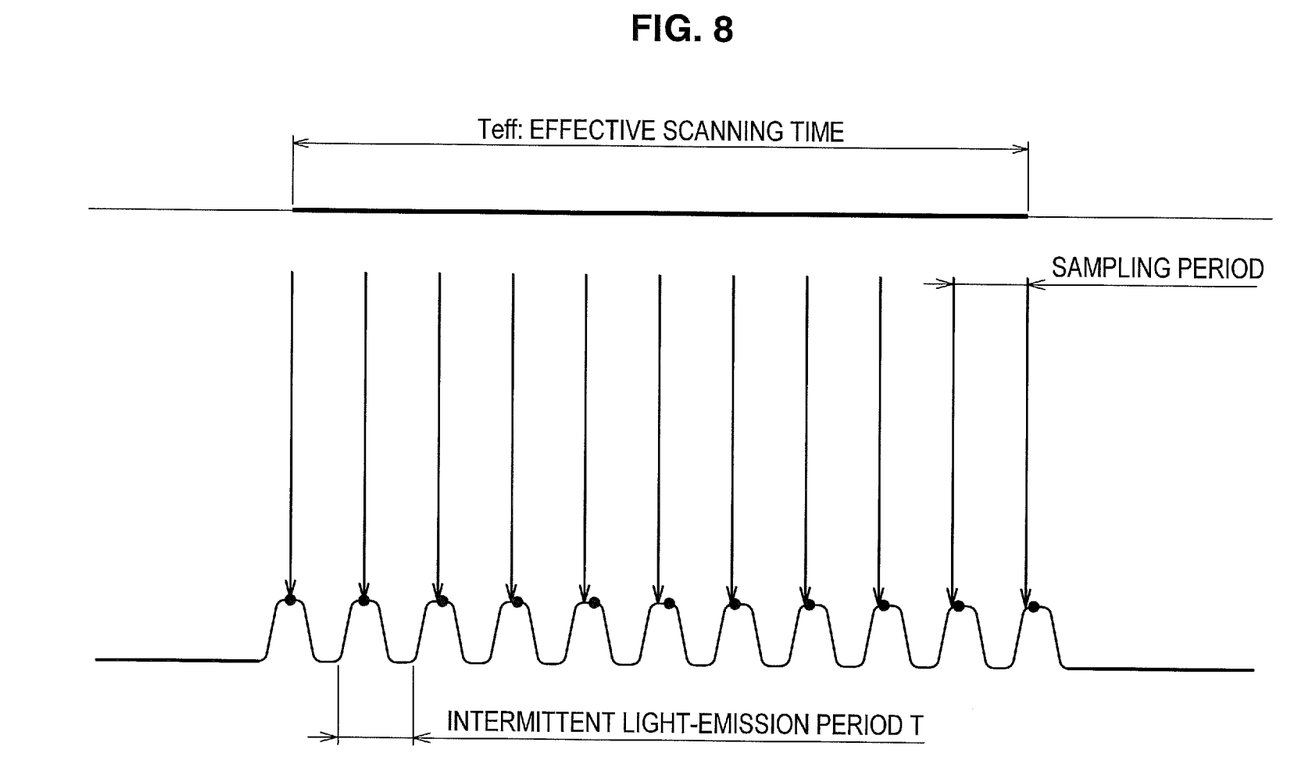
FIG. 8 is a schematic diagram illustrating a case in which a sampling period is caused to be identical to an intermittent light-emission period T.

The detector 110 such as a photomultiplier tube (PMT) detecting photons is an analog element and photoelectrically converts introduced photons into an electric signal (a current value or a voltage value). The converted electric signal is subjected to A/D conversion at a predetermined sampling period. The signal subjected to the A/D conversion corresponds to one-pixel image information. FIGS. 6 to 8 are diagrams illustrating characteristics of the sampling period and an intermittent light-emission period T by the pulse waveform P1.

FIG. 6 illustrates a case in which the sampling period is shorter than the intermittent light-emission period T. In other words, FIG. 6 illustrates a case in which the sampling frequency is higher than the intermittent light-emission frequency. In the characteristics in the lower portion of FIG. 6, characteristics indicated by a solid line represent the electric signal after the photoelectric conversion performed by the detector 110 and a dashed line indicates the characteristics connecting the sampling values. In this case, since sampling is performed at a non-light-emission timing, that is, a non-excited timing, in some cases, an obtained image is an image (a patched pattern-like image, i.e., a so-called teeth-missing image), in which brightness and darkness alternate in adjacent pixels.

FIG. 7 illustrates a case in which the sampling period is longer than the intermittent light-emission period T. In other words, FIG. 7 illustrates a case in which the sampling frequency is lower than the intermittent light-emission frequency. As in FIG. 6, characteristics indicated by a solid line represent the electric signal after the photoelectric conversion performed by the detector 110 and a dashed line indicates the characteristics connecting the sampling values. In this case, the electric signal after the photoelectric conversion includes an electric signal with a frequency higher than the sampling frequency. Therefore, although the electric signal is originally a constant-level signal, various values are sampled, and thus a correct waveform may not be reproduced due to the influence of aliasing. Thus, when the sampling period and the intermittent light-emission period T are asynchronous, the signal level is not constant. Also, when the sampling period and the intermittent light-emission period T are synchronous, the original signal level is constant. However, in the asynchronous case, color deterioration occurs due to unnecessary excitation. When a biological object is observed, an adverse effect such as unnecessary excitation or extinction of cells or the like to be observed due to phototoxicity may also occur.

FIG. 8 illustrates a case in which the sampling period is caused to be identical to the intermittent light-emission period T. That is, FIG. 8 illustrates a case in which the sampling frequency is identical to the intermittent light-emission frequency. In FIG. 8, the phases are caused to be identical so that sampling is performed at the peak of the intermittent light-emission period T. Thus, when the sampling period is synchronized with the intermittent light-emission period T, a correct signal can be obtained and the color deterioration can also be suppressed to be as small as possible.

The sampling frequency fs is, for example, in the range of about 100 kHz to about 10 MHz. Basically, the sampling frequency fs is decided from the specification of the microscope system 1000 and the intermittent light-emission frequency is caused to be identical to the sampling frequency fs. On the other hand, the intermittent light-emission frequency may be first decided and the sampling frequency may be caused to be identical to the intermittent light-emission frequency.

Also, pulse light emission other than the above description, an ON/OFF signal of a scanning beam, or an ON/OFF signal of image acquisition are also preferably synchronized with the sampling period of the A/D conversion, but may not necessarily be synchronized.

To cause the sampling period to be identical to the intermittent light-emission period T, an ON/OFF period by the optical amplifier unit 240 in FIG. 1 is considered to be identical to the sampling period of the A/D conversion circuit that performs A/D conversion on the electric signal detected by the detector 110 such as a photomultiplier tube (PMT). That is, by inputting the same ON/OFF clock by the SOA driver 244 to the A/D conversion circuit without change, it is possible to cause the sampling period to be identical to the intermittent light-emission period T reliably. Thus, the frequencies and the phases related to the sampling and the intermittent light emission can be caused to be identical.

As described in FIG. 2, the laser beam L3 output from the wavelength conversion module 250 is emitted in a pulse shape within a light-emission period of the intermittent light emission. FIG. 8 illustrates light emission after the pulse is processed to the degree that the pulse is not seen by the lowpass filter (the lowpass filter 318 illustrated in FIG. 1). At this time, as will be described in detail below, the band limitation of the lowpass filter is preferably equal to or less than ½ of the sampling frequency. For example, when the sampling frequency is 1 MHz, the band limitation of the lowpass filter is set to a maximum of 500 kHz. In this way, it is possible to establish the Nyquist sampling theorem. Accordingly, phase deviation between the sampling period and the intermittent driving period is permitted.

[5. Example of Configuration in Which Sampling Period is Caused to be Identical to Intermittent Driving Period]

Next, a configuration by which the sampling period and the intermittent driving period are caused to be identical will be described with reference to FIG. 1. As illustrated in FIG. 1, the control unit 300 is configured to include a timing generator 302, a sampling signal generation unit 304, an A/D conversion unit 306, a memory 308, a galvano-beam control unit 310, a D/A conversion unit 312, an intermittent light-emission signal generation unit 314, an oscillation synchronization signal injection unit 316, and the lowpass filter (LPF) 318.

As illustrated in FIG. 1, the timing generator 302 generates a clock CLK and the sampling signal generation unit 304 generates a sampling signal with the sampling frequency fs based on the clock CLK. Also, the intermittent light-emission signal generation unit 314 generates an intermittent light-emission signal with a period T for intermittent light emission based on the clock CLK. Thus, the sampling signal generated by the sampling signal generation unit 340 and the intermittent light-emission signal generated by the intermittent light-emission signal generation unit 314 can be caused to be synchronized. For example, when the sampling signal generation unit 304 uses the clock CLK as the sampling frequency fs without change and the intermittent light-emission signal generation unit 314 uses the clock CLK as the frequency of the intermittent light-emission signal without change, the sampling period and the intermittent light-emission period T become identical.

The electric signal obtained through the photoelectric conversion by the detector 110 is input to the lowpass filter 318. The lowpass filter 318 performs the band limitation on the input signal so that the Nyquist sampling theorem is established, as described above, and outputs the signal to the A/D conversion unit 306. The A/D conversion unit 306 performs the A/D conversion on the input signal at the sampling frequency fs. The SOA driver 244 turns the laser beam (the pulse waveform L1) on and off at the frequency of the intermittent light-emission signal and outputs the intermittent laser beam (the pulse waveform L2).

Also, the galvano-beam control unit 310 receives an input of the clock signal CLK from the timing generator 302 and generates a galvanomirror control signal to control the galvanomirrors 120 and 130. The galvanomirror control signal is subjected to D/A conversion by the D/A conversion unit 312, and the galvanomirrors 120 and 130 are controlled by the galvanomirror control signal subjected to the D/A conversion. Thus, the galvanomirrors 120 and 130 can also be controlled based on the clock CLK. As described above, in the raster scanning scheme, the light source 200 is caused to emit light only during the effective scanning time $T_{eff}$. Therefore, the intermittent light-emission signal generation unit 314 generates the intermittent light-emission signal only during the effective scanning time $T_{eff}$ of the raster scanning based on the clock CLK and turns the intermittent light-emission signal off during a time other than the effective scanning time $T_{eff}$. Likewise, the sampling signal generation unit 304 generates the sampling signal only during the effective scanning time $T_{eff}$ based on the clock CLK. Accordingly, the sampling signal and the intermittent light-emission signal become synchronized at an operation period of the galvanomirrors. Thus, by turning the sampling signal and the intermittent light-emission signal off during a time other than the effective scanning time $T_{eff}$, the average power can be lowered and the peak power can thus be increased.

[6. Configuration of Lowpass Filter]

The lowpass filter 318 installed on the front stage of the A/D conversion unit 306 performs the band limitation on an output of the detector (PMT) 110 to a frequency satisfying the Nyquist sampling theorem. More specifically, the lowpass filter 318 performs the band limitation of the output of the detector 110 to a frequency of ½ to ⅓ of the sampling frequency. For example, when the sampling frequency is 1 GHz, the output of the detector 110 is subjected to the band limitation to about 300 kHz to about 500 kHz. When the sampling frequency is variable, the band of the lowpass filter 318 is also changed in proportion to the sampling frequency.

By performing the band limitation on the output of the detector 110 to a frequency satisfying the Nyquist sampling theorem, it is possible to prevent an unnecessary signal from being included in a sampling result reliably and thus to improve reproduction of an image reliably.

[7. Synchronization Between Oscillation Optical Pulse of Laser Beam and Modulation of Laser Beam]

Next, a relation between an oscillation optical pulse of a laser beam and the period of an intermittent light-emission signal will be described. In the embodiment, the oscillation optical pulse of the laser beam can also be synchronized with the clock CLK of the timing generator 302.

The oscillation frequency of the laser beam radiated from the mode-locked laser unit 220 is decided by the speed of light and the path length of the external resonator described above. The signal injected from the timing generator 302 is also considered to have almost the same as the frequency as the frequency of the resonator. However, by providing phase information which the system has through the injection of the transmission synchronization signal from the oscillation synchronization signal injection unit 316, it is possible to synchronize the phase information which the system has with the external resonator.

Therefore, the oscillation synchronization signal injection unit 316 sends the oscillation synchronization signal synchronized with the clock CLK to a capacitor of a bias Tee based on the clock signal CLK of the timing generator 302. The oscillation synchronization signal is supplied as an AC component of a gain current Ig for the semiconductor laser 222.

Since the oscillation synchronization signal synchronized with the clock CLK is supplied as the AC component of the gain current Ig for the semiconductor laser 222, the oscillation optical pulse of the laser beam radiated from the semiconductor laser 222 can be synchronized with the clock CLK.

As described above, the oscillation synchronization signal injection unit 316 supplies the semiconductor laser 222 with the oscillation synchronization signal synchronized with the clock CLK. Thus, it is possible to synchronize the oscillation optical pulse of the laser beam radiated from the semiconductor laser 222 with the clock CLK.

As described above, the intermittent light-emission signal generation unit 314 generates the intermittent light-emission signal for the intermittent light emission based on the clock CLK and drives the optical amplifier unit 240 using the intermittent light-emission signal, the optical amplifier unit 240 is turned on and off to be driven in synchronization with the clock CLK and the laser beam is modulated in synchronization with the clock CLK. Accordingly, it is possible to synchronize the oscillation optical pulse of the laser beam radiated from the semiconductor laser 222 with the modulation of the laser beam. Thus, even when the laser beam has a considerably high pulse optical frequency, it is possible to easily synchronize the oscillation optical pulse of the laser beam with the modulation of the laser beam and thus to acquire a desired image.

Also, the synchronization of the oscillation optical pulse of the laser beam by the oscillation synchronization signal injection unit 316 is optional, and the synchronization may not be performed. In particular, when the period of the oscillation optical pulse of the laser beam and the period of the intermittent light-emission signal are considerably different, a desired image can be acquired without performing the synchronization.

[8. Relation Between Optical Resolution and Sampling Frequency]

The resolution of a laser scanning microscope is decided by an optical resolution proportional to a wavelength $\lambda$ [m] of an excitation light source. The optical resolution do is estimated to be $\lambda/2$ or $0.61*\lambda$. However, for simplicity, when $\lambda/2$ is used, the optical resolution do=500 nm in the case of "$\lambda$=1000 nm." When there is no limitation on the band of a photoelectric conversion element, an electric resolution de is decided by a beam speed v [m/s] and the sampling frequency fs [1/s].

In the electric resolution de, the sampling interval [m]=1/2 of v/fs by the Nyquist sampling theorem, and thus, the electric resolution "de=v/(2*fs)" can be calculated.

The beam speed v [m/s] can be calculated from a reciprocation frequency of the scanning beam and a scanning range. Therefore, when the calculation is performed based on the reciprocation frequency of 500 Hz and the scanning range of 1 mm as representative numbers, "v=1 [m/s]" is obtained by scanning the range of 1 mm at 1 ms which is half of the period of 2 ms.

As a result, the electric resolution de becomes "de=1 [m/s]/(2*1E+6[1/2])=500 nm" at "fs=1 MHz," and thus is identical to the optical resolution do.

As described above, even when the beam speed is caused to be 10 times faster, 10 MHz suffices for the sampling frequency and it can be understood that there is no advantage from causing the sampling frequency to be any faster. Accordingly, in Japanese Patent No. 5007092, it is difficult to obtain the advantages described in the embodiment. Even when high-speed sampling is performed in synchronization with the pulse light emission, the resolution is not improved and it is also difficult to increase a signal amount.

According to the embodiment, as described above, by intermittently emitting the laser beam from the light source 200, the period of the intermittent light emission is configured to be identical to the sampling period of the electric signal of the image obtained from the detector 110. Thus, it is possible to reliably prevent a patched pattern-like image, i.e., a teeth-missing image, from being acquired. Also, it is possible to reliably prevent a correct waveform from not being reproduced due to the influence of aliasing. Further, since the unnecessary excitation of the laser beam can be suppressed, it is also possible to prevent an adverse effect such as extinction of cells or the like to be observed due to phototoxicity The preferred embodiments of the present disclosure have been described above in detail with reference to the appended drawings, but embodiments of the present disclosure are not limited to the technical scope of the present disclosure. It should be apparent to those skilled in the art that various modifications or corrections may occur within the technical scope described in the claims and are, of course, understood to pertain to the technical scope of the present disclosure.

Additionally, the present application may also be configured as below.

(1) A laser scanning microscope system including:
a mode-locked laser unit configured to radiate a laser beam with a predetermined frequency;
an intermittent light-emitting unit configured to intermittently emit the laser beam radiated from the mode-locked laser unit in a predetermined intermittent light-emission period;
a detector configured to convert a fluorescent substance into an electric signal, the fluorescent substance receiving the intermittently emitted laser beam and then being excited from an object; and
an A/D conversion unit configured to sample the electric signal in a sampling period synchronized with the intermittent light-emission period.

(2) The laser scanning microscope system according to (1), wherein frequencies and phases related to the sampling and the intermittent light emission are the same.

(3) The laser scanning microscope system according to (1), wherein the mode-locked laser unit radiates the laser beam for two-photon excitation.

(4) The laser scanning microscope system according to (1), wherein a sampling signal providing the sampling period to the A/D conversion unit and an intermittent light-emission signal providing the intermittent light-emission period to the intermittent light-emitting unit are the same signal.

(5) The laser scanning microscope system according to (1), further including:
a sampling signal generation unit configured to generate a sampling signal providing the sampling period to the A/D conversion unit; and
an intermittent light-emission signal generation unit configured to generate an intermittent light-emission signal providing the intermittent light-emission period to the intermittent light-emitting unit,
wherein the sampling signal and the intermittent light-emission signal are generated based on an identical clock.

(6) The laser scanning microscope system according to (1), wherein the mode-locked laser unit or the intermittent light-emitting unit causes the laser beam to be incident on the object only during a predetermined effective light-emission period.

(7) The laser scanning microscope system according to (6), further including:
a first galvanomirror configured to perform scanning with the laser beam in a first direction of a surface of the object;
a second galvanomirror configured to perform scanning with the laser beam in a second direction orthogonal to the first direction of the surface of the object; and
a galvanomirror control unit configured to control the first galvanomirror and the second galvanomirror,
wherein, when the scanning in the first direction is completed, the galvanomirror control unit returns the laser beam to a start position of the first direction and performs the scanning in the second direction by one line of the laser beam, and then performs the scanning in the first direction again, and
wherein the effective light-emission period is at least a part of a period in which the scanning in the first direction is performed.

(8) The laser scanning microscope system according to (1), further including:
a lowpass filter configured to perform band limitation on the electric signal output from the detector and to input the electric signal to the A/D conversion unit,
wherein the lowpass filter performs the band limitation in a manner that a Nyquist sampling theorem is established for a frequency of the sampling.

(9) The laser scanning microscope system according to (8), wherein the lowpass filter performs the band limitation in a manner that the band limitation is equal to or less than ½ of the frequency of the sampling.

It should be understood that various changes and modifications to the presently preferred embodiments described The invention is claimed as follows:

1. A laser scanning microscope system comprising:
a mode-locked laser unit configured to radiate a laser beam with a predetermined frequency;
an intermittent light-emitting unit configured to intermittently emit the laser beam radiated from the mode-locked laser unit in an intermittent light-emission period to an object;
a detector configured to convert a fluorescent signal from the object into an electric signal, the fluorescent signal is generated by the intermittently emitted laser beam; and
an A/D conversion unit configured to sample the electric signal in a sampling period same as the intermittent light-emission period,
wherein the mode-locked laser unit or the intermittent light-emitting unit is configured to cause the laser beam to be incident on the object only in the intermittent light-emission period having a same time period as the sampling period.

2. The laser scanning microscope system according to claim 1, wherein frequencies and phases related to the sampling and the intermittent light emission are the same.

3. The laser scanning microscope system according to claim 1, wherein the mode-locked laser unit is configured to radiate the laser beam for two-photon excitation.

4. The laser scanning microscope system according to claim 1, wherein a sampling signal providing the sampling period to the A/D conversion unit and an intermittent light-emission signal providing the intermittent light-emission period to the intermittent light-emitting unit are the same signal.

5. The laser scanning microscope system according to claim 1, further comprising:
a sampling signal generation unit configured to generate a sampling signal providing the sampling period to the A/D conversion unit; and
an intermittent light-emission signal generation unit configured to generate an intermittent light-emission signal providing the intermittent light-emission period to the intermittent light-emitting unit,
wherein the sampling signal and the intermittent light-emission signal are generated based on an identical clock.

6. The laser scanning microscope system according to claim 1, further comprising:
a first galvanomirror configured to perform scanning with the laser beam in a first direction of a surface of the object;
a second galvanomirror configured to perform scanning with the laser beam in a second direction orthogonal to the first direction of the surface of the object; and
a galvanomirror control unit configured to control the first galvanomirror and the second galvanomirror,
wherein, when the scanning in the first direction is completed, the galvanomirror control unit returns the laser beam to a start position of the first direction and performs the scanning in the second direction by one line of the laser beam, and then performs the scanning in the first direction again, and
wherein the intermittent light-emission period is at least a part of a period in which the scanning in the first direction is performed.

7. The laser scanning microscope system according to claim 1, further comprising:
a lowpass filter configured to perform band limitation on the electric signal output from the detector and to input the electric signal to the A/D conversion unit,
wherein the lowpass filter is configured to perform the band limitation in a manner that a Nyquist sampling theorem is established for a frequency of the sampling.

8. The laser scanning microscope system according to claim 7, wherein the lowpass filter is configured to perform the band limitation in a manner that the band limitation is equal to or less than ½ of the frequency of the sampling.

9. The laser scanning microscope system according to claim 1, further comprising an optical amplifier, wherein the optical amplifier is configured to amplify and modulate the laser beam from the mode-locked laser unit.

* * * * *